(12) United States Patent
Balestracci

(10) Patent No.: US 6,190,362 B1
(45) Date of Patent: *Feb. 20, 2001

(54) PLUNGER ROD

(75) Inventor: Ernest Balestracci, Iselin, NJ (US)

(73) Assignee: Bracco Diagnostics, Inc., Princeton, NJ (US)

( * ) Notice: Under 35 U.S.C. 154(b), the term of this patent shall be extended for 0 days.

This patent is subject to a terminal disclaimer.

(21) Appl. No.: 09/542,522

(22) Filed: Apr. 3, 2000

Related U.S. Application Data

(63) Continuation-in-part of application No. 09/408,242, filed on Sep. 29, 1999, which is a continuation-in-part of application No. 09/273,901, filed on Mar. 22, 1999, now Pat. No. 6,030,367.

(51) Int. Cl.$^7$ .................................................. A61M 5/315

(52) U.S. Cl. ............................................. 604/218; 604/220

(58) Field of Search .................................... 604/218, 232, 604/207, 187, 228, 181, 227, 101

(56) References Cited

U.S. PATENT DOCUMENTS

| D. 403,762 | 1/1999 | Gabbard et al. ................... D24/113 |
| 4,543,093 | 9/1985 | Christinger ............................ 604/228 |
| 5,411,488 | 5/1995 | Pagay et al. .......................... 604/218 |
| 5,700,247 | 12/1997 | Grimard et al. ...................... 604/220 |
| 5,860,961 | 1/1999 | Gettig ..................................... 604/199 |
| 5,989,219 | * 11/1999 | Villas et al. .......................... 604/110 |
| 6,059,756 | * 5/2000 | Yeh ........................................ 604/218 |
| 6,093,170 | * 7/2000 | Hsu et al. .............................. 604/110 |

FOREIGN PATENT DOCUMENTS

| WO 91/00114 | 1/1991 | (WO) ................................. 604/218 |
| WO 90/09827 | 5/1993 | (WO) ................................. 604/229 |

\* cited by examiner

*Primary Examiner*—Sharon Kennedy
*Assistant Examiner*—Jennifer Maynard
(74) *Attorney, Agent, or Firm*—Imre Balogh

(57) ABSTRACT

Dimensionally stable plunger rod for use with a plunger in a cartridge or syringe barrel for manual or power-assisted withdrawal of fluid from a site or expelling fluid from the cartridge or syringe barrel having:

a plunger rod body with a distal and a proximal end;

an end disc at the distal end;

a threaded member integral with the end disc designed to engage a plunger;

a thumb rest at the proximal end;

a central disc at the mid point between the end disc and the thumb rest to provide additional reinforcement to the plunger rod;

four longitudinal radially extending rectangular vanes connected to the end disc at the distal end, to the central disc at the mid point, and to the thumb rest at the proximal end;

two pairs of longitudinal radially extending reinforcing vanes forming two triangular configurations with one of the longitudinal radially extending rectangular vanes on one side of the plunger rod body; and two pairs of longitudinal radially extending reinforcing vanes forming two triangular configurations with another of the longitudinal radially extending rectangular vanes on the opposite side of the plunger rod body, each of the pairs of the reinforcing vanes are connected to the end disc at the distal end, to the central disc at the mid point, and to the thumb rest at the proximal end.

7 Claims, 15 Drawing Sheets

FIG. 1 - PRIOR ART
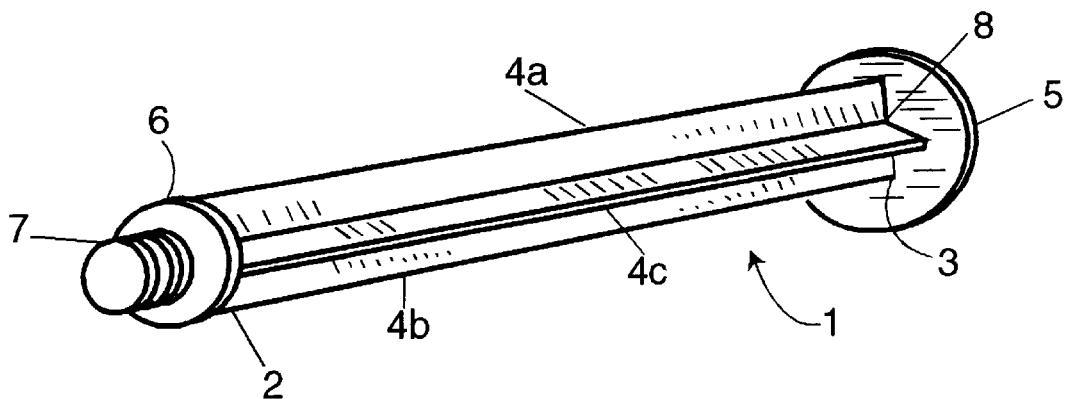
FIG. 2 - PRIOR ART
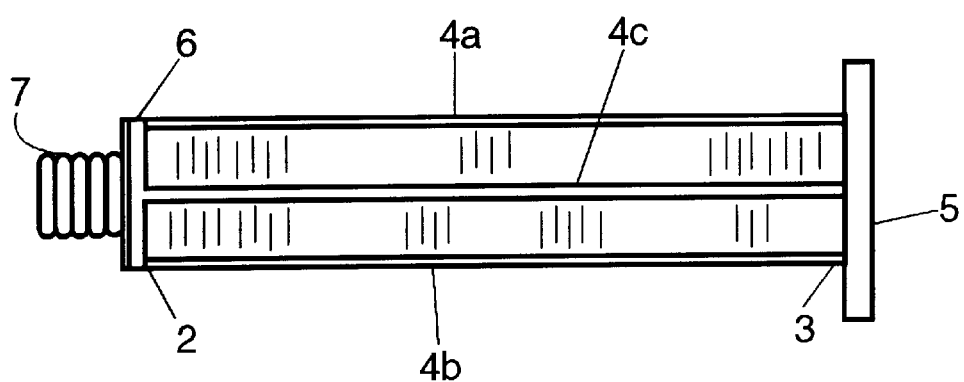

FIG. 3 - PRIOR ART
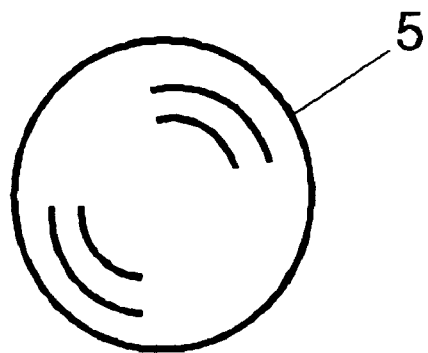
FIG. 4 - PRIOR ART
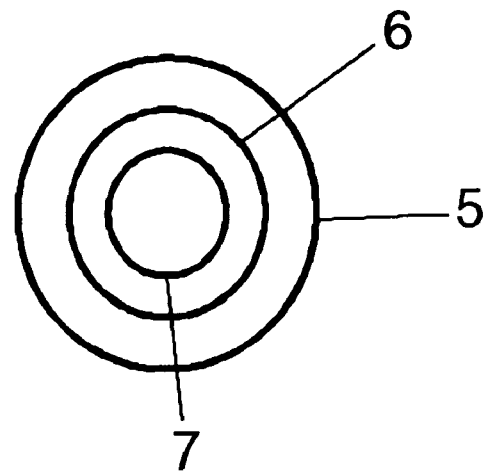

FIG. 11
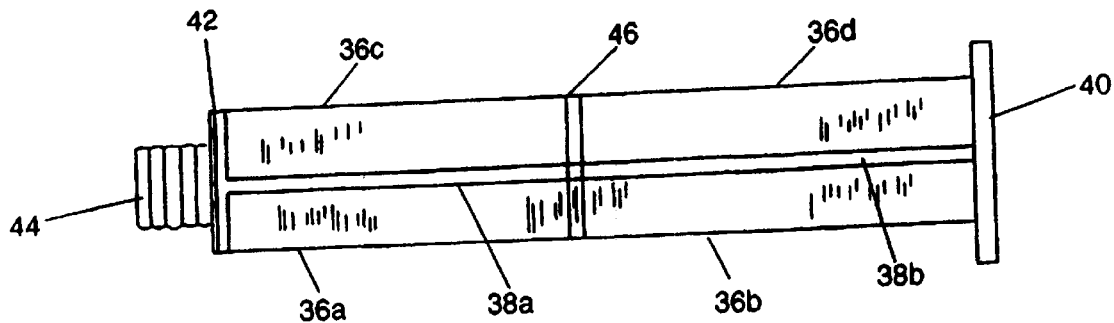
FIG. 12
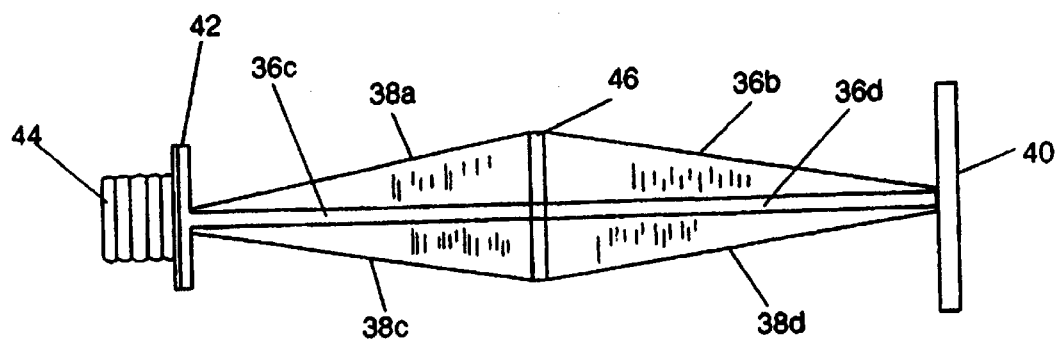
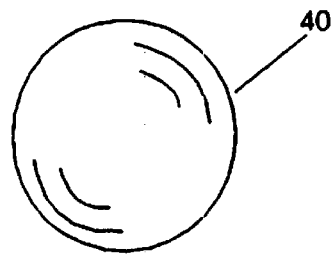
FIG. 13
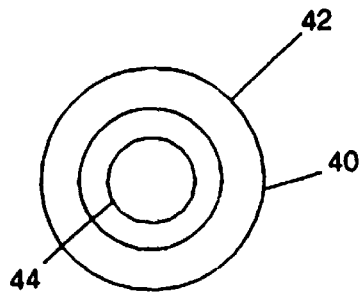
FIG. 14

PLUNGER ROD

This application is a continuation-in-part of application Ser. No. 09/408,242 filed on Sep. 29, 1999, which in turn is a continuation-in-part of application Ser. No. 09/273,901 filed on Mar. 22, 1999, now U.S. Pat. No. 6,030,367.

BACKGROUND OF THE INVENTION

1. Field of the Invention

The present invention relates to a plunger rod for use in a syringe or cartridge barrel having a plunger and containing a parenteral solution therein, or in a syringe or cartridge which are empty and are to be filled with a parenteral solution by the user at the time of administration.

The present invention also i-elates to a plunger rod for use in a syringe or cartridge containing a parenteral solution therein intended to be dispensed from a power injector.

2. Reported Developments

Syringes are cartridges made of glass or polymeric materials for dispensing parenteral solutions or withdrawing biological fluids from a patient are well known in the prior art. They comprise a cylindrical barrel with a tapered end at one end to which a needle or luer connector can be attached, and an open end which is stoppered by a plunger of a resilient thermoplastic or elastomeric material. The plunger serves the function of a stopper, when the barrel is filled with a fluid, or as a slidable member to expel the fluid from the barrel or to withdraw a biological fluid from a patient or another source.

In order to expel fluid from the barrel or to withdraw fluid into the barrel, the plunger is moved toward the distal end or toward the proximal end of the barrel by a plunger rod which is attachable to the plunger typically by screw threads. The user exerts a force, manually or by the use of a power injector, on the plunger rod to push and pull the plunger in the barrel. While the plunger rod does not contact the fluid in the barrel, it provides a very important function: it causes the plunger to move in an axial direction back and forth in the barrel when an external force is applied thereon.

The force applied to the plunger by the plunger rod should be perpendicular to the plunger so that the force exerted on the wall of the barrel by the plunger is uniform around the 360° of its cylindrical configuration. To wit, the direction of movement of the plunger rod should always be perpendicular to the surface of the plunger. When the plunger rod flexes in the barrel, the direction of force on the plunger will not be uniform resulting in pressure points at certain areas of contact between the plunger and the inside wall of the barrel and, conversely, inadequate pressure points at other parts of the interface between the plunger and the inside wall of the barrel. Such pressure differences tend to allow leakage and difficulty in moving the plunger at an even rate in the barrel.

Recognizing the importance of dimensional stability, the prior art has incorporated various stability enhancing means into plunger rods which include the following.

The assembly disclosed in U.S. Pat. No. 4,543,093 has a plunger rod the central portion of which is almost as large as the inside diameter of the syringe barrel so that is will assist in keeping the plunger rod assembly concentrically aligned within the syringe barrel.

WO93/09827 discloses a shank having a plurality of longitudinal and radially extending vanes. In one preferred embodiment the shank is provided with four vanes in an "X" pattern while in another preferred embodiment the shank is provided with three vanes forming a "Y" pattern.

U.S. Pat. Nos. 5,700,247 and 5,860,961 disclose plunger rods having a plurality of vanes or support ribs.

A common feature of these plunger rods is a shank extending between the distal and proximal ends of the plunger rods having vanes or support ribs thereon. The vanes or support ribs are identical with one another running longitudinally on the shank and extending radially therefrom.

I have now discovered a strong, dimensionally stable plunger rod which is of novel configuration and is useful in combination with plungers intended for use in a syringe or cartridge barrel for manual or power injections.

SUMMARY OF THE INVENTION

The present invention provides a strong, dimensionally stable plunger rod designed for use in a cartridge or syringe barrel having a plunger therein for withdrawing fluid from a site or expelling fluid from the barrel of a cartridge or syringe. The plunger rod may be used in manual or power-assisted fluid withdrawal or delivery systems.

The plunger rod of the present invention has four embodiments, two of which are characterized by the presence of a reinforcing disc at about the longitudinal mid point of the plunger rod. The third embodiment of the present invention is characterized by the presence of four longitudinal radially extending veins supported by a first pair of longitudinal radially extending reinforcing vanes and a second pair of longitudinal radially extending reinforcing vanes. The forth embodiment of the present invention is characterized by the presence of four longitudinal radially extending rectangular vanes and four longitudinal radially extending supporting vanes forming an hourglass shape surface and having a reinforcing disc at about the longitudinal mid point of the plunger rod.

The first embodiment of the plunger rod having a distal end and a proximal end comprises:
an end disc at the distal end;
a threaded member integral with the end disc designed to engage a plunger;
a thumb rest at the proximal end for facilitating exertion of external pressure on the plunger rod;
a reinforcing disc at about the longitudinal mid point of the plunger rod;
a first pair of rectangular radially extending vanes connecting the end disc and the reinforcing disc;
a second pair of rectangular radially extending vanes connecting the reinforcing disc and the thumb rest;
a first pair of isosceles triangular radially extending vanes connecting the end disc an the reinforcing disc, wherein the smallest angle of the isosceles triangular vanes point toward the reinforcing disc; and
a second pair of isosceles triangular radially extending vanes connecting the reinforcing disc and the thumb rest, wherein the smallest angle of the isosceles triangular vanes point toward the reinforcing disc;
wherein:
said first pair of said rectangular radially extending vanes and said first pair of said isosceles triangular radially extending vanes are integral with each other and with said end disc and said reinforcing disc; and
said second pair of said rectangular radially extending vanes and said second pair of said isosceles triangular radially extending vanes are integral with each other and with said reinforcing disc and said thumb rest.

The second embodiment of the plunger rod having a distal end and a proximal end comprises:
- an end disc at the distal end;
- a threaded member integral with the end disc designed to engage a plunger;
- a thumb rest at the proximal end for facilitating exertion of external pressure on the plunger rod;
- a reinforcing disc at about the longitudinal mid point of the plunger rod;
- a first pair of rectangular radially extending vanes connecting the end disc and the reinforcing disc;
- a second pair of rectangular radially extending vanes connecting the reinforcing disc and the thumb rest;
- a first pair of isosceles triangular radially extending vanes connecting the end disc and the reinforcing disc wherein the smallest angle of the isosceles triangular vanes point toward the thumb rest;
- wherein;
  - said first pair of said rectangular radially extending vanes and said first pair of said isosceles triangular radially extending vanes are integral with each other and with said end disc and said reinforcing disc; and
  - said second pair of said rectangular radially extending vanes and said second pair of said isosceles triangular radially extending vanes are integral with each other and with said reinforcing disc and said thumb rest.

The third embodiment of the plunger rod having first, second, third and fourth sides, a distal end and a proximal end comprises:
- an end disc at the distal end;
- a threaded member integral with the end disc designed to engage a plunger;
- a thumb rest at the proximal end for facilitating exertion of external pressure on the plunger rod;
- four longitudinal radially extending rectangular vanes spaced 90° from each other and connected to the end disc and to the thumb rest;
- on the first side of said plunger rod:
- a first pair of longitudinal radially extending reinforcing vanes;
- a second pair of longitudinal radially extending reinforcing vanes, both the first pair and the second pair of longitudinal radially extending reinforcing vanes being connected to the end disc and to the thumb rest;
- on the third side opposite to said first side of said plunger rod:
- a first pair of longitudinal radially extending reinforcing vanes; a second pair of longitudinal radially extending reinforcing vanes, both the first pair and the second pair of longitudinal radially extending reinforcing vanes being connected to the end disc and to the thumb rest;
- wherein:
  - each of said first and second pairs of the longitudinal radially extending reinforcing vanes on the first side of the plunger rod, and each of said first and second pairs of the longitudinal radially extending reinforcing vanes on the third side of said plunger rod forms an obtuse triangle with one of the longitudinal radially extending rectangular vanes, wherein the obtuse angle of the so-formed triangle is at the mid point between the end disc and thumb rest;
- on the second side of said plunger rod:
- a first pair of longitudinal radially extending reinforcing vanes forming a two-dimensional hourglass-shape surface extending from the end disc to the thumb rest;
- on the fourth side of said plunger rod:
- a second pair of longitudinal radially extending reinforcing vanes forming a two-dimensional hourglass-shape surface extending from the end disc to the thumb rest.

The fourth embodiment of the plunger rod having first, second, third and fourth sides, a distal end and a proximal end comprises:
- an end disc at the distal end;
- a threaded member integral with the end disc designed to engage a plunger;
- a thumb rest at the proximal end for facilitating exertion of external pressure on the plunger rod;
- a central disc at about the mid point between the end disc and the thumb rest to provide additional reinforcement between the end disc and the thumb rest;
- four longitudinal radially extending rectangular vanes spaced about 90° from each other and connected to the end disc, the central disc and to the thumb rest;
- on the first side of said plunger rod:
- a first pair of longitudinal radially extending reinforcing vanes;
- a second pair of longitudinal radially extending reinforcing vanes, both the first pair and the second pair of longitudinal radially extending reinforcing vanes being connected to the end disc, the central disc and to the thumb rest;
- on the third side opposite to said first side of said plunger rod:
- a first pair of longitudinal radially extending reinforcing vanes;
- a second pair of longitudinal radially extending reinforcing vanes, both of said first pair and said second pair of longitudinal radially extending reinforcing vanes being connected to said end disc, the central disc and to the thumb rest;
- wherein:
  - each of said first pair and each of said second pair of longitudinal radially extending reinforcing vanes on the first side of said plunger rod and each of said first pair and each of said second pair of the longitudinal radially extending reinforcing vanes on the third side of said plunger rod forms an obtuse triangle with one of the longitudinal radially extending rectangular vanes, wherein the obtuse angle of said triangle is at the mid point between said end disc and said thumb rest;
- on the second side of said plunger rod:
- a first pair of longitudinal radially extending reinforcing vanes forming a two-dimensional hourglass-shape surface extending from the end disc to the central disc, and from the central disc to the thumb rest;
- on the fourth side of the plunger rod: a second pair of longitudinal radially extending reinforcing vanes forming a two-dimensional hourglass-shape surface extending from the end disc to the central disc, and from the central disc to the thumb rest.

BRIEF DESCRIPTION OF THE DRAWINGS

FIG. 1 is a perspective view of a typical prior art plunger rod;

FIG. 2 is a side-elevation view thereof;

FIG. 3 is a bottom plan view thereof;

FIG. 4 is a top plan view thereof;

FIG. 11 is a side-elevational view of the plunger rod shown in FIG. 10;

FIG. 12 is another side-elevational view of the plunger rod shown in FIG. 10 rotated 90° from that shown in FIG. 11;

FIG. 13 is a bottom plan view of the plunger rod shown in FIG. 10;

FIG. 14 is a top plan view of the plunger rod shown in FIG. 10;

DETAILED DESCRIPTION OF THE INVENTION

Figure 5:
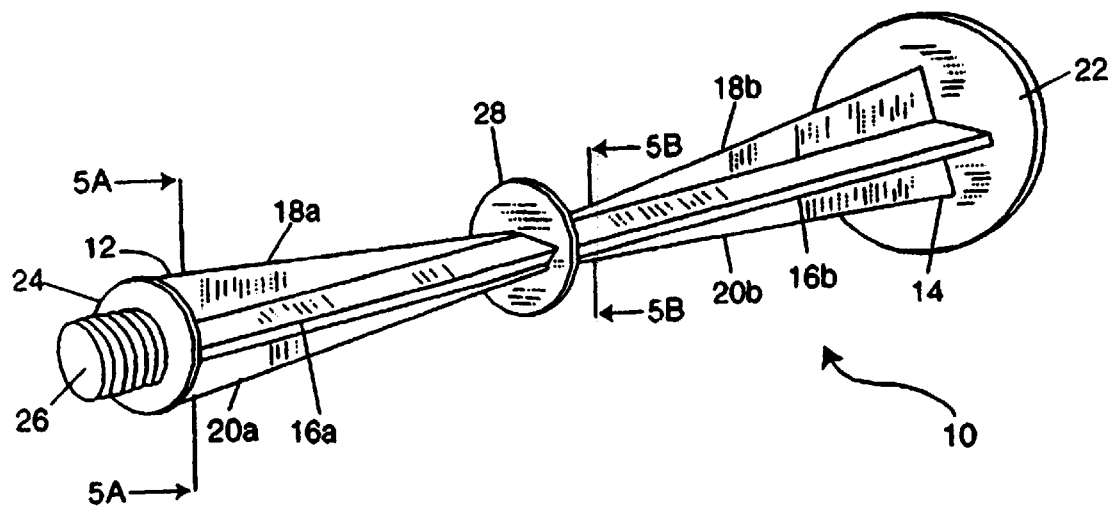
FIG. 5 is a perspective view of the first embodiment of the plunger rod of the present invention.

Referring to FIGS. 1–4, a typical prior art plunger rod is shown in perspective, side-elevational, bottom plan and top plan views. Plunger rod 1 having a distal end 2 and a proximal end 3 comprises: longitudinal and radially extending vanes 4, 4b, 4c and 4d (4d is hidden in the perspective view); a thumb rest 5 at the proximal end 3 and a disc 6 at the distal end 2 of the plunger rod; and a screw threaded member 7 extending from disc 6 designed to engage a plunger. As shown, vanes 4a, 4b, 4c and 4d are equivalent to one another extending from thumb rest 5 to disc 6. These vanes meeting at the center 8 of the plunger rod are of rectangular configuration.

Referring now to the first embodiment of the present invention shown in FIGS. 5–9, the configuration of the plunger rod is atypical compared to the plunger rod shown in FIGS. 1–4. Plunger rod 10 having a distal end 12 and a proximal end 14 comprises:

Longitudinal radially extending vanes 16a and 16b (16c and 16d are hidden in FIG. 5) having a rectangular configuration; longitudinal radially extending vanes 18a, 18b, 20a and 20b having a triangular configuration; a thumb rest 22 at the proximal end of the plunger rod 10; a disc 24 at the distal end 12 of the plunger rod; a screw threaded member 26 extending from disc 24 designed to engage a plunger; and a central disc 28 located at about the mid point between thumb rest 22 and disc 24.

As shown in the drawings, central disc 28 supports the rectangular vanes and the triangular vanes and is integral therewith to provide dimensional stability to the plunger rod. Cross sectional view of FIG. 5A illustrates that at the proximal end 12 of the plunger rod the rectangular and triangular vanes are of about equal in size in the radial direction, however, while the rectangular vanes connecting to central disc 28 maintain their rectangular configuration, the triangular vanes diminish in size in the radial direction into central disc 28 and merge with both the rectangular vanes and the central disc. Cross-sectional view of the plunger rod in FIG. 5B shows that rectangular vane 16b is the same size as rectangular vane 16a shown in cross-sectional view in FIG. 5A, while triangular vane 18b diminishes to a small size and merges with rectangular vane 16b.

Figure 5A:
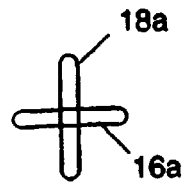
FIG. 5A is a cross-sectional view of the plunge rod taken along the line 5A—5A of FIG. 5.
Figure 5B:
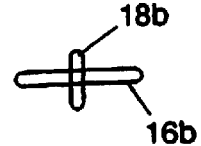
FIG. 5B is another cross-sectional view of the plunger rod taken along the line 5B—5B of FIG. 5.
Figure 6:
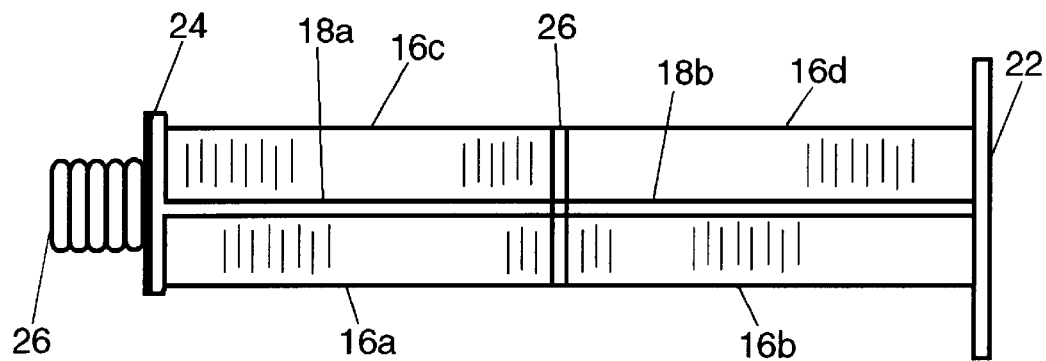
FIG. 6 is a side-elevational view of the plunge rod shown in FIG. 5.

FIG. 6 shows the plunger rod of FIG. 5 in a side-elevational view where triangular vanes 18a and 18b are at the center of the Fig., and rectangular vanes 16a, 16b, 16c and 16d are at the sides of the Fig.

Figure 7:
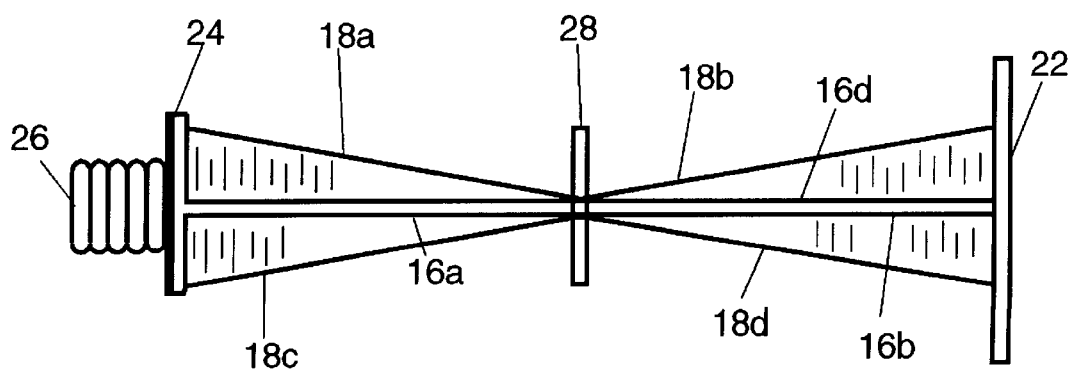
FIG. 7 is another side-elevational view of the plunger rod shown in FIG. 5 rotated 90° from that shown in FIG. 6.
Figure 8:
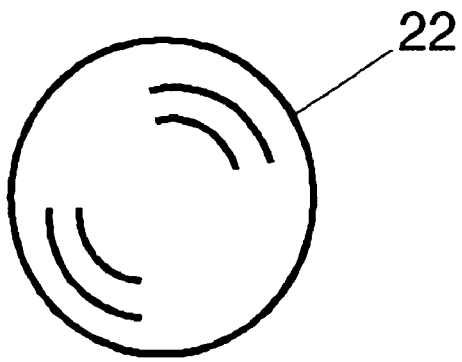
FIG. 8 is a bottom plan view of the plunge rod shown in FIG. 5.
Figure 9:
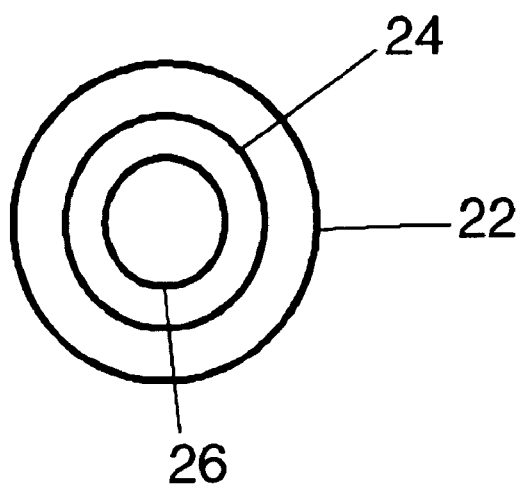
FIG. 9 is a top plan view of the plunger rod shown in FIG. 5.

FIG. 7 is another side-elevational view of the plunger rod of FIG. 5 rotated 90° from that shown in FIG. 6. Here, triangular vanes 18a, 18b, 18c and 18d are at the sides of the Fig. and rectangular vanes 16a and 16b are at the center thereof FIGS. 8 and 9 show respectively the bottom and top plan views of the plunger rod.

FIGS. 10–14 show the second embodiment of the present invention wherein the orientation of the triangular vanes are reversed to that shown in FIGS. 5–9.

Plunger rod 30 having a distal end 32 and a proximal end 34 comprises:

longitudinal radially extending vanes 36a and 36b (36c and 36d are hidden in FIG. 10) having a rectangular configuration;

longitudinal radially extending vanes 38a, 38b, 38c and 38d having triangular configuration; thumb rest 40 at the proximal end 34 of plunger rod 30;

a disc 42 at the distal end 32 of the plunger rod;

a screw threaded member 44 extending form the disc 42 designed to engage a plunger;

and a central disc 46 located at about the mid point between thumb rest 40 and disc 42.

Figure 10:
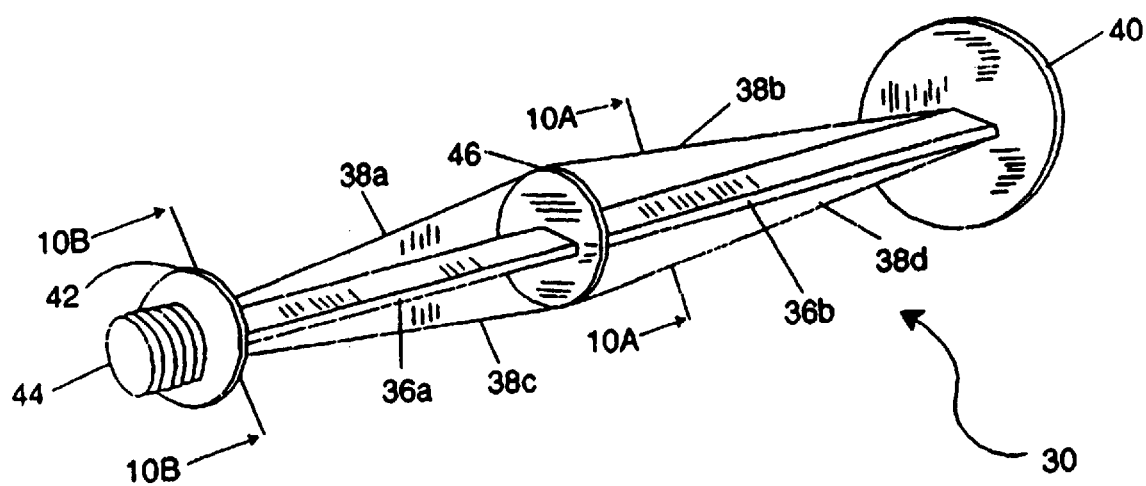
FIG. 10 is a perspective view of the second embodiment of the plunge rod of the present invention.
Figure 10A:
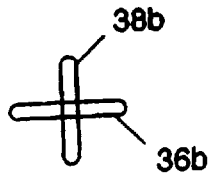
FIG. 10A is a cross-sectional view of the plunger rod taken along the line 10A—10A of FIG. 10.
Figure 10B:
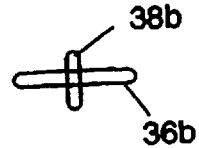
FIG. 10B is a cross-sectional view of the plunger rod taken along the line 10B—10B of FIG. 10.

Central disc 46 supports the rectangular vanes and the triangular vanes and is integral therewith to provide dimensional stability to the plunger rod. Cross sectional view FIG. 10A, taken along the line 10A—10A of FIG. 10 illustrates that at about the mid point of the plunger rod the rectangular and triangular vanes are about equal in size in the radial direction, however, while the rectangular vanes connecting to the central disc 46, disc 42 and thumb rest 40 maintain their rectangular configuration, the triangular vanes diminish in size in the radial direction as they approach disc 42 and thumb rest 40. As shown, the triangular vanes merge with the rectangular vanes at disc 42 and thumb rest 40. Cross-sectional view of the plunger rod in FIG. 10B, taken along the line 10B—10B of FIG. 10, shows that triangular vanes 38a, 38b, 38c and 38d diminish to a small size and merge with rectangular vanes 36a and 36b at disc 42 and thumb rest 40.

FIG. 11 shows the plunger rod of FIG. 10 in a side-elevational view where triangular vanes 38 and 38b are at the center of the Fig., and rectangular vanes 36a, 36b, 36c and 36d are at the sides of the Fig.

FIG. 12 is another side elevational view of the plunger rod of FIG. 10 rotated 90° from that shown in FIG. 11. The triangular vanes 38a, 38b, 38c and 38d are at the sides of the Fig. and rectangular vanes 36c and 36d are at the center thereof.

FIGS. 13 and 14 show respectively the bottom and top plan views of the plunger rod.

Reference is now being made to the third embodiment of the present invention shown in FIGS. 15–19. The plunger rod, generally designated by the numeral 50, includes four longitudinal radially extending rectangular vanes 60a, 60b, 60c and 60d as best seen in FIG. 15B. These vanes meet at a center line or axis 61. The vanes are integral with each other at the axis and have a distal end 52 and a proximal end 54. At the distal end the vanes terminate in a disc 56; at the proximal end 54 the vanes terminate in a thumb rest 58. A screw-threaded member 64 extends from disc 56 designed to engage a plunger. Disc 56, thumb rest 58, screw threaded member 64 used in cooperation with the longitudinal radially extending rectangular vanes 60a, 60b, 60c and 60d constitute a typical prior art plunger rod.

In addition to having the above-described components, the present invention incorporates reinforcing or supporting members in the plunger rod which reinforcing or supporting members comprise:

a first pair of longitudinal radially extending supporting vanes; and a second pair of longitudinal radially extending supporting vanes; both the first pair and the second pair of vanes being connected to disc 56 at the distal end 62 and to thumb rest 58 at the proximal end 54 of plunger rod 50.

Figure 15:
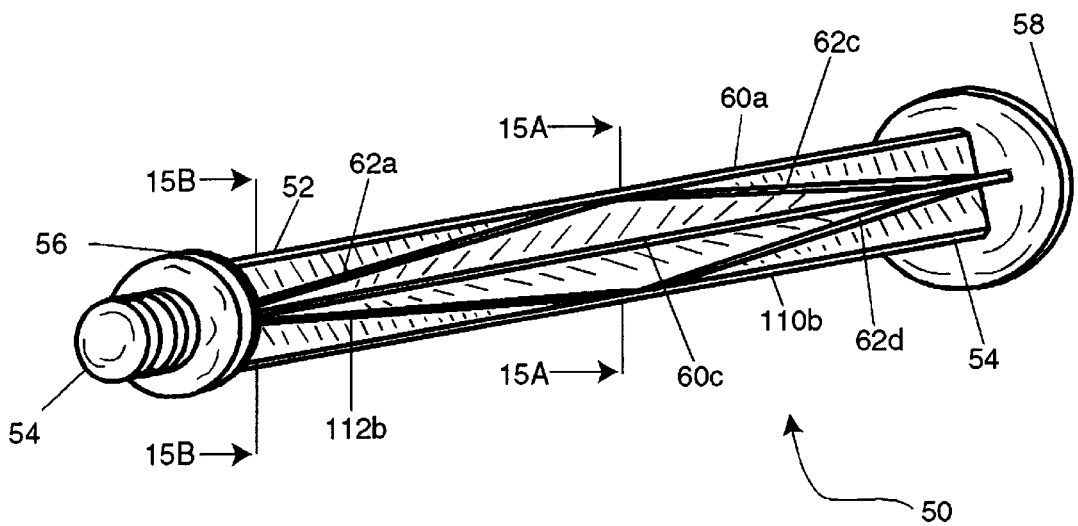
FIG. 15 is a perspective view of the third embodiment of the plunger rod of the present invention.
Figure 15B:
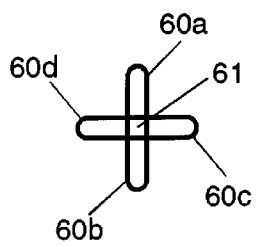
FIG. 15B is a cross-sectional view of the plunger rod taken along the line 15B—15B of FIG. 15.
Figure 15A:
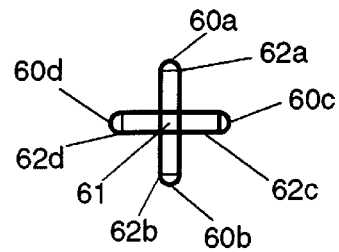
FIG. 15A is a cross-sectional view of the plunger rod taken along the line 15A—15A of FIG. 15.

FIG. 15A shows a cross-sectional view of plunger rod 50 taken along the line 15A—15A of FIG. 15, wherein: the numerals 60a, 60b, 60c, and 60d denote the longitudinal radially extending vanes; the numerals 62a, 62b, 62c and 62d denote the longitudinal radially extending supporting vanes; and the numeral 61 denotes the central axis at which the longitudinal radially extending rectangular vanes meet.

Figure 16:
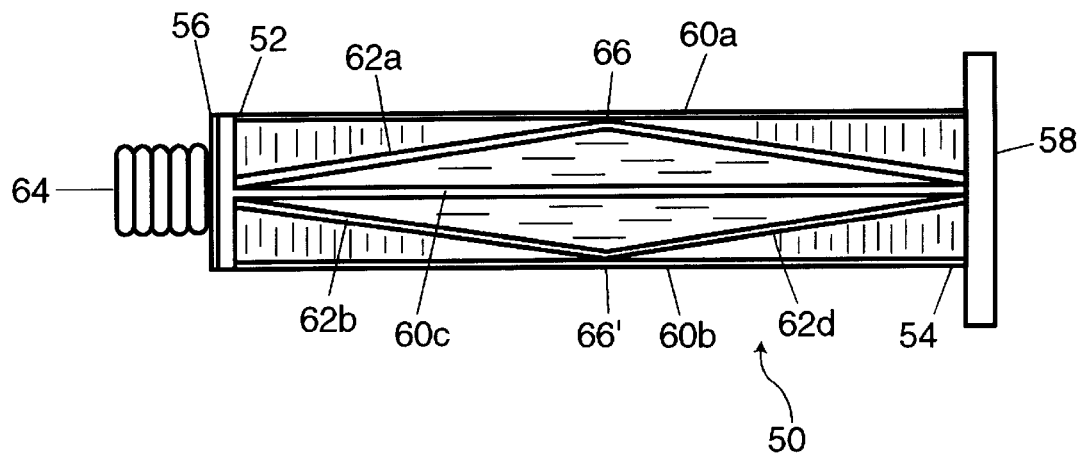
FIG. 16 is a side-elevational view of the plunger rod shown in FIG. 15.

The first pair of longitudinal radially extending supporting vanes: 62a and 62c; and 62b and 62d form two obtuse triangles with the longitudinal radially extending supporting vane 60c, wherein the obtuse angles of the triangles are at or approximately at the mid points 66 and 66' between disc 56 and thumb rest 58 as best seen in FIG. 16.

Figure 16A:
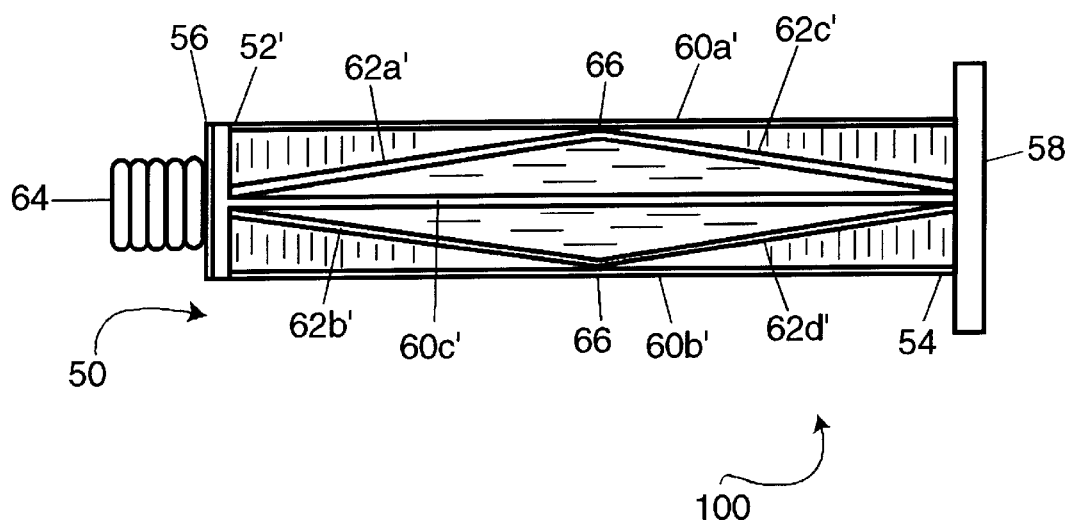
FIG. 16A is another side elevational view of the plunger rod shown in FIG. 15 rotated 180° from that shown in FIG. 16.

When side-elevational view of plunger rod 50 shown in FIG. 16 is rotated 180°, the opposite side, or mirror image side, is shown thereof in FIG. 16A wherein like numbers correspond with the numerals shown in FIG. 16 and are distinguished therefrom by the marks ' or ".

Figure 17:
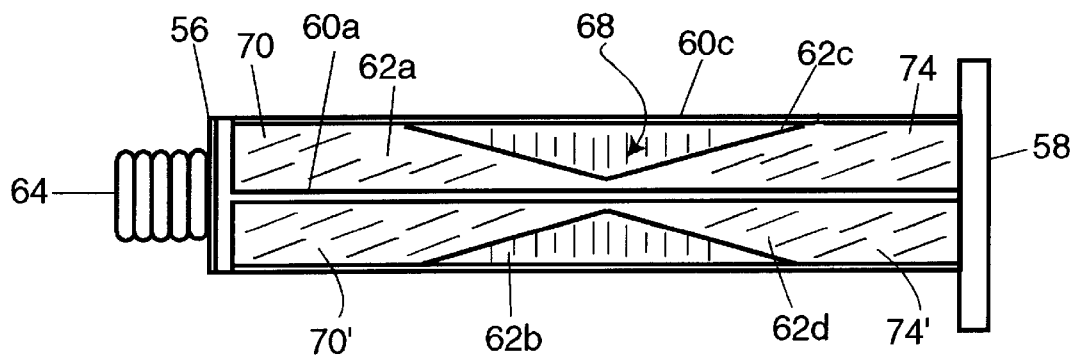
FIG. 17 is another side-elevational view of the plunger rod of FIG. 15 rotated 90° from that shown in FIG. 16.

Turning now to another side-elevational view of plunger rod 50, FIG. 17 shows a side-elevational view of plunger rod 50, rotated 90° from that of the side-elevational view shown in FIG. 16. As shown in FIG. 17, first pair of longitudinal radially extending supporting vanes: 62a and 62C; and 62b and 62d together form a two-dimensional hourglass-shape surface. Longitudinal radially extending vane 60a runs through the center portion of the radially extending two-dimensional hourglass-shape surface connecting disc 56 and thumb rest 58. The hourglass-shape surface constricts into a channel generally designated with the numeral 68 at or approximately at the mid point between disc 56 and thumb rest 58. Distal end 70 and 70' and proximal end 74 and 74' of the hourglass-shape surface extend to disc 56 and thumb rest 58 and merge with longitudinal radially extending vane 60a.

Figure 17A:
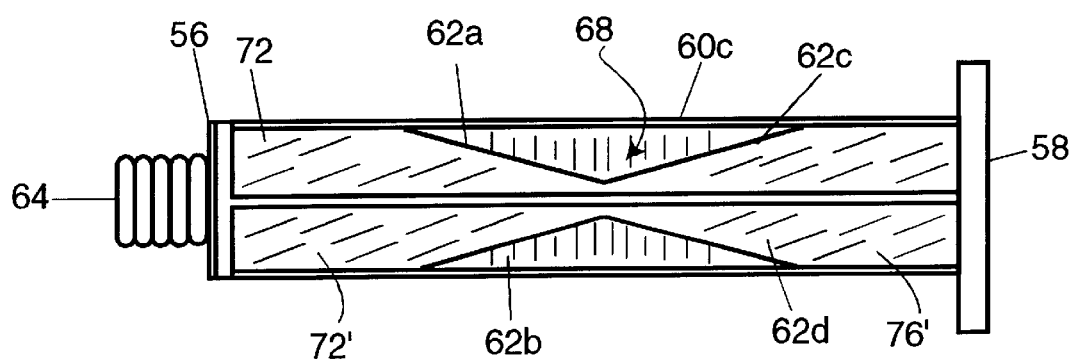
FIG. 17A is another side-elevational view of the plunger rod shown in FIG. 15 rotated 180° from that shown in FIG. 17.
Figure 18:
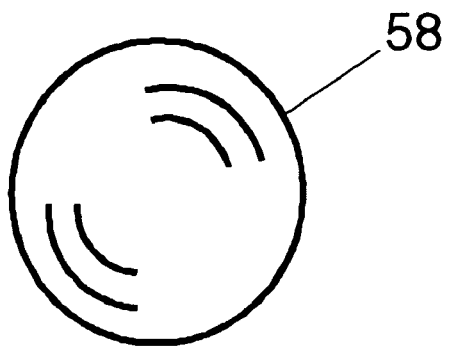
FIG. 18 is a bottom plan view of the plunger rod shown in FIG. 15.
Figure 19:
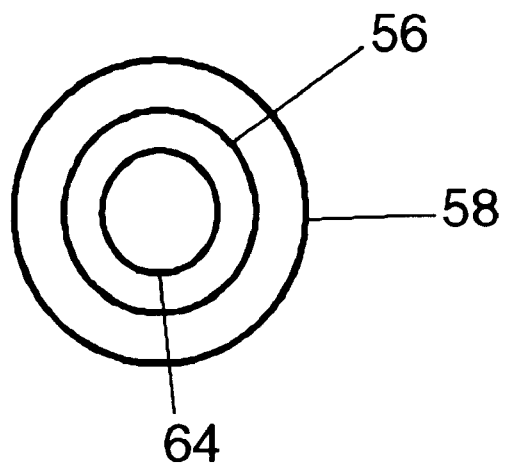
FIG. 19 is a top plan view of the plunger rod shown in FIG. 15.

When side elevational view of plunger rod 50 shown in FIG. 17 is rotated 180°, the opposite side, or mirror image side, of the plunger rod is shown in FIG. 17A wherein: the numeral 68' denotes a channel into which the hourglass surface constricts; the numerals 70, 70', 72 and 72' denote the distal ends of the hourglass-shape surface; and the numerals 74, 74', 76 and 76' denote the proximal ends of the hourglass-shape surface.

Reference is now being made to the fourth embodiment of the present invention shown in FIGS. 20–24. The plunger rod, generally designated by the numeral 80, includes four longitudinal radially extending rectangular vanes 90a, 90b, 90c and 90d as best seen in FIG. 20B. These vanes meet at a center line or axis 91. The vanes are integral with each other at the axis and have a distal end 82 and a proximal end 84. At the distal end the vanes terminate in a disc 86; at the proximal end 84 the vanes terminate in a thumb rest 88. A screw-threaded member 94 extends from disc 86 designed to engage a plunger. Disc 86, thumb rest 88, screw threaded member 94 used in cooperation with the longitudinal radially extending rectangular vanes 90a, 90b, 90c and 90d constitute a typical prior art plunger rod.

In addition to having the above-described components, the present invention incorporates reinforcing or supporting members in the plunger rod which reinforcing or supporting members comprise:

a first pair of longitudinal radially extending supporting vanes; and a second pair of longitudinal radially extending supporting vanes; both the first pair and the second pair of supporting vanes being connected to disc 86 at the distal end 92 and to thumb rest 88 at the proximal end 84 of plunger rod 80. At the mid point between disc 86 and thumb rest 88 a central disc 87 is positioned supporting the longitudinal radially extending rectangular vanes and the first and second pairs of the longitudinal radially extending supporting vanes. The central disc, the longitudinal radially extending rectangular vanes, and the longitudinal radially extending supporting vanes are integral with each other and provide a strong, dimensionally stable plunger rod for both manual and power assisted injection systems.

Figure 20:
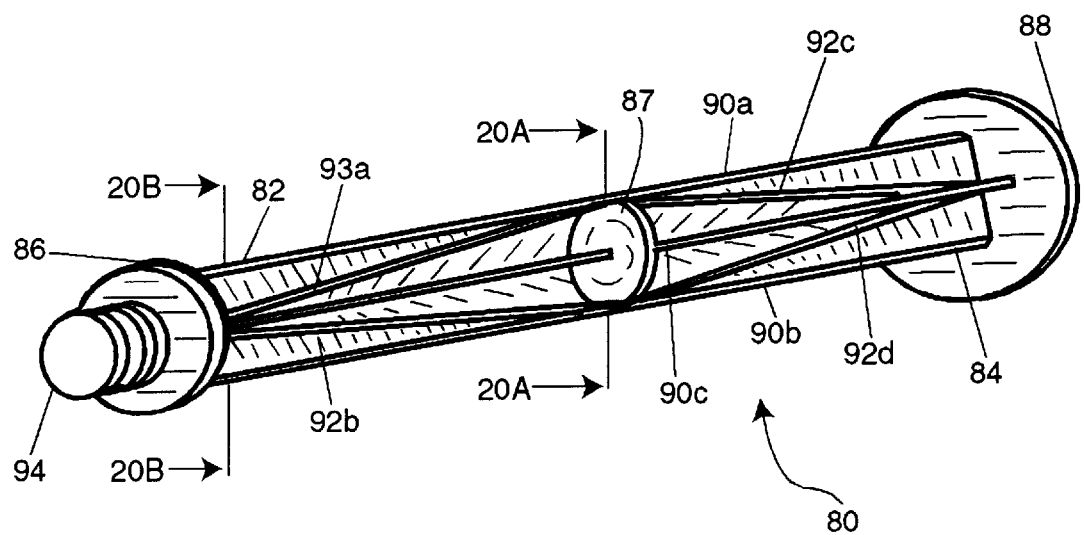
FIG. 20 is a perspective view of the fourth embodiment of the plunger rod of the present invention.
Figure 20B:
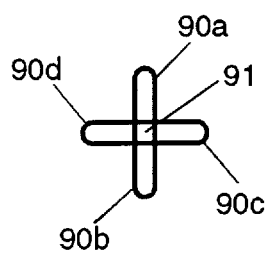
FIG. 20B is a cross-sectional view of the plunger rod taken along the line 20B—20B of FIG. 20.
Figure 20A:
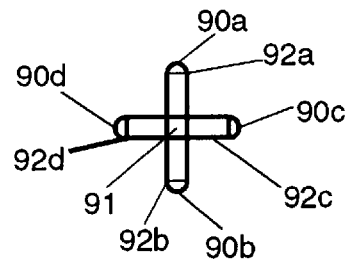
FIG. 20A is a cross-sectional view of the plunger rod taken along the line 20A—20A of FIG. 20.

FIG. 20A shows a cross-sectional view of plunger rod 80 taken along the line 20A—20A of FIG. 20, wherein: the numerals 90a, 90b, 90c, and 90d denote the longitudinal radially extending rectangular vanes; the numerals 92a, 92b, 92c and 92d denote the longitudinal radially extending supporting vanes; and the numeral 91 denotes the central axis at which the longitudinal radially extending rectangular vanes meet.

Figure 21:
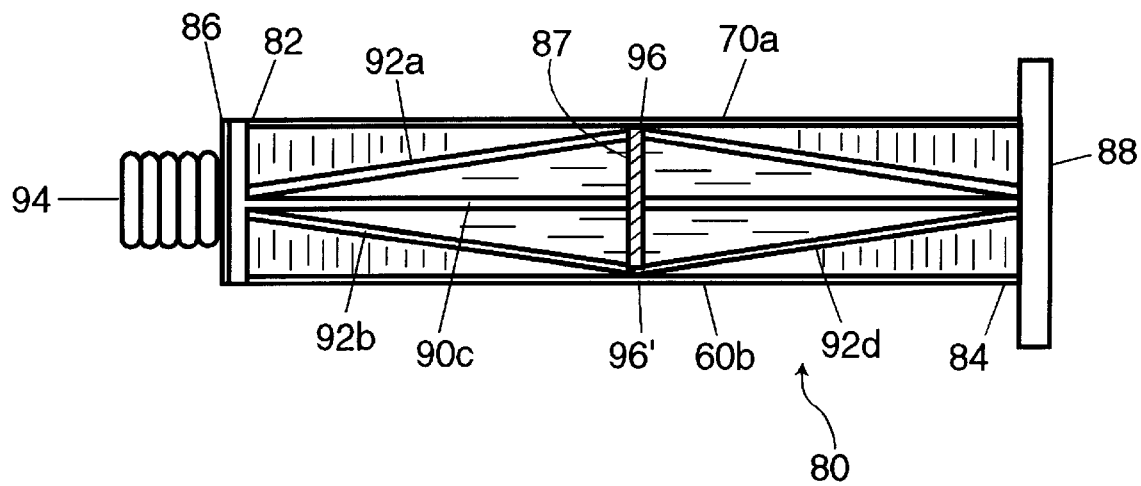
FIG. 21 is another side-elevational view of the plunge rod shown in FIG. 20 rotated 180° from that shown in FIG. 21.

The first pair of longitudinal radially extending supporting vanes: 92a and 92c; and 92b and 92d form two obtuse triangles with the longitudinal radially extending rectangular vane 90c, wherein the obtuse angles of the triangles are at or approximately at the mid points 96 and 96' between disc 86 and thumb rest 88 as best seen in FIG. 21.

Figure 21A:
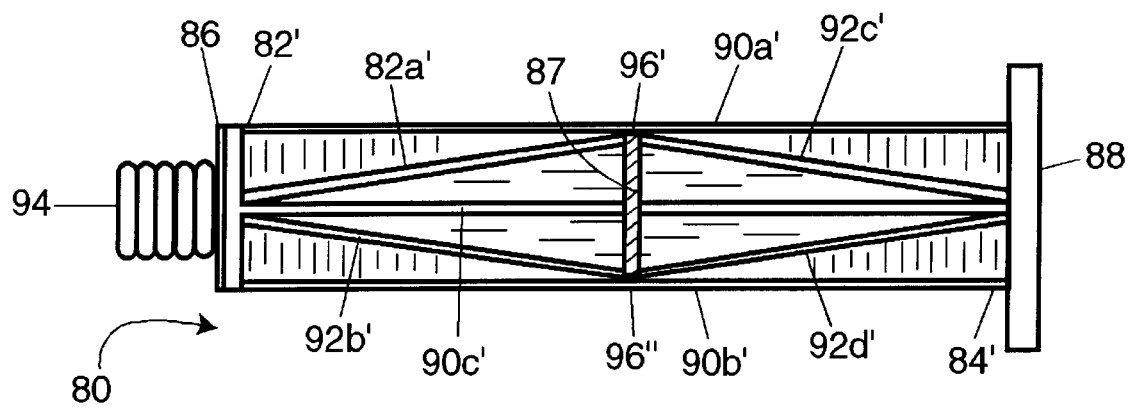

When side-elevational view of plunger rod 80 shown in FIG. 21 is rotated 180°, the opposite side, or mirror image side, is shown thereof in FIG. 21A wherein like numbers correspond with the numerals shown in FIG. 21 and are distinguished therefrom by the marks ' or ".

Figure 22:
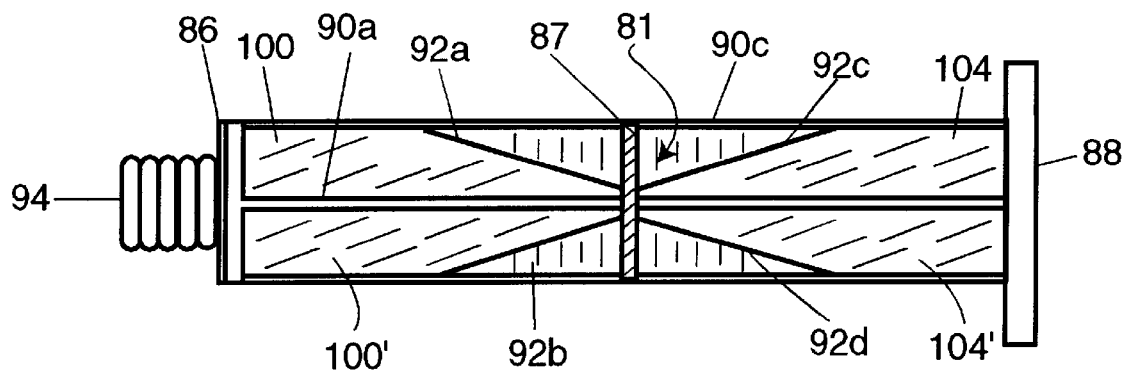
FIG. 22 is another side-elevational view of the plunger rod shown in FIG. 20 rotated 90° from that shown in FIG. 20.

Turning now to another side-elevational view of plunger rod 80, FIG. 22 shows a side-elevational view of plunger rod 80, rotated 90° from that of the side-elevational view shown in FIG. 21. As shown in FIG. 22, first pair of longitudinal radially extending supporting vanes: 92a and 92C; and 92b and 92d together form a two-dimensional hourglass-shape surface. Longitudinal radially extending rectangular vane 90a runs through the center portion of the radially extending two-dimensional hourglass-shape surface connecting disc 86 and thumb rest 88. The hourglass-shape surface constricts into a channel generally designated with the numeral 81 at or approximately at the mid point between disc 86 and thumb rest 88. Central disc 81 supports the hourglass-shape surface at its constricted channel 81. Distal end 100 and 100' and proximal end 104 and 104' of the hourglass-shape surface extend to disc 86 and thumb rest 88 and merge with longitudinal radially extending rectangular vane 90a.

Figure 22A:
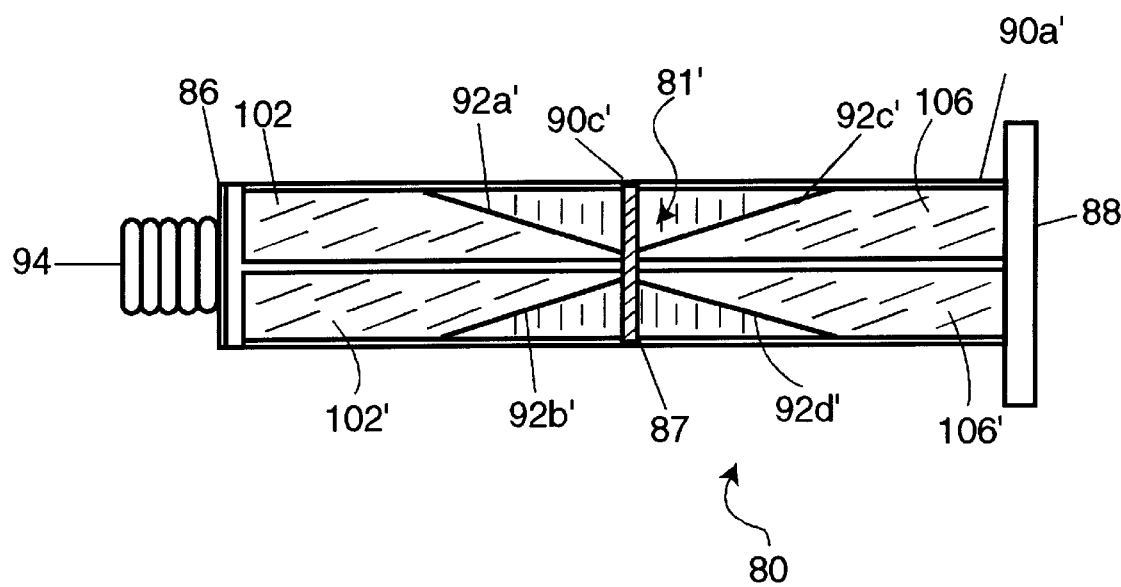
FIG. 22A is another side-elevational view of the plunger rod shown in FIG. 20 rotated 180° from that shown in FIG. 22.
Figure 23:
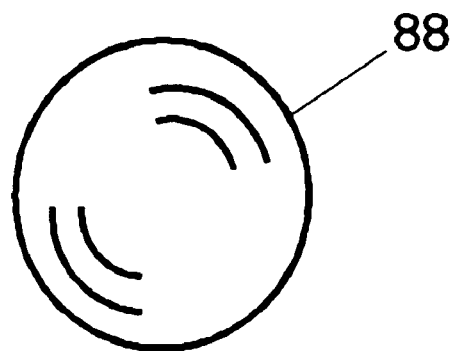
FIG. 23 is a bottom plan view of the plunger rod shown in FIG. 20.
Figure 24:
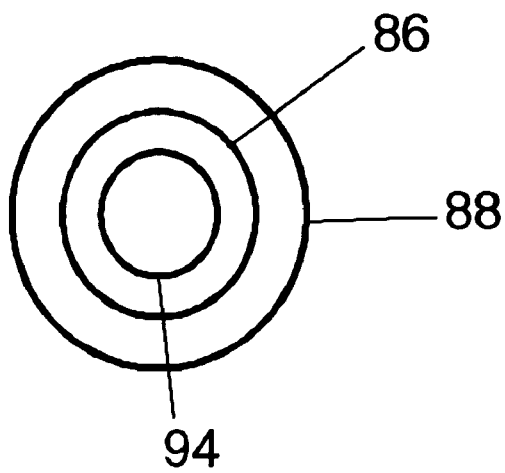
FIG. 24 is a top plan view of the plunger rod shown in FIG. 20.

When the side elevational view of plunger rod 80 shown in FIG. 22 is rotated 180°, the opposite side, or mirror image side, of the plunger rod is shown in FIG. 22A wherein: the numeral 98' denotes a channel into which the hourglass surface constricts; the numerals 100, 100', 102 and 102' denote the distal ends of the hourglass-shape surface; and the numerals 104, 104', 106 and 106' denote the proximal ends of the hourglass-shape surface.

The plunger rod of the present is made by injection molding which is well-known in the art using thermoplastic materials. Polypropylene, polyethylene and blend thereof are preferred for providing strength to the plunger rod. However, other polymers, such as polystyrenes, polyesters and polycarbonates may also be used.

| Parts List | |
|---|---|
| Prior art: | |
| Plunger rod | 1 |
| Distal end of plunger rod | 2 |
| Proximal end of plunger rod | 3 |
| Vanes | 4a, 4b, 4c and 4d |
| Thumb rest | 5 |
| Disc | 6 |

| -continued | |
|---|---|
| Parts List | |
| Screw threaded member | 7 |
| Center where vanes meet | 8 |
| Present invention (First embodiment): | |
| Plunger rod | 10 |
| Distal end of plunger rod | 12 |
| Proximal end of plunger rod | 14 |
| Vanes having triangular configuration | 16a, 16b, 16c and 16d |
| Thumb rest | 22 |
| Disc at the distal end of plunger rod | 24 |
| Threaded member | 26 |
| Central disc in plunger rod | 28 |
| Present invention (Second embodiment): | |
| Plunger rod | 30 |
| Distal end of plunger rod | 32 |
| Proximal end of plunger rod | 34 |
| Rectangular vanes | 36a, 36b, 36c and 36d |
| Triangular vanes | 38a, 38b, 38c and 38d |
| Thumb rest | 40 |
| Disc at distal end | 42 |
| Screw threaded member | 44 |
| Central disc in plunger rod | 46 |
| Present invention (Third embodiment): | |
| Plunger rod, generally designated | 50 |
| Distal end of plunger rod | 52 |
| Proximal end of plunger rod | 54 |
| Disc at distal end | 56 |
| Thumb rest at proximal end | 58 |
| Longitudinal radially extending vanes | 60a, 60b, 60c and 60d |
| Center line or axis | 61 |
| First pair of longitudinal radially extending supporting vanes | 62a, 62b, 62c, and 62d |
| Second pair of longitudinal radially extending supporting vanes | 62a', 62b', 62c', and 62d' |
| Channel in hourglass-shape surface | 68, 68' |
| Distal end of hourglass-shape surface | 70, 70', 72, 72' |
| Proximal end of hourglass-shape surface | 74, 74', 76, 76' |
| Present invention (Fourth embodiment) | |
| Plunger rod | 80 |
| Longitudinal radially extending rectangular vanes | 90a, 90b, 90c and 90d |
| Center lines or axis | 91 |
| Distal end of radially extending rectangular vanes | 82 |
| Proximal end of radially extending rectangular vanes | 84 |
| Disc at distal end | 86 |
| Thumb rest | 88 |
| Central disc | 81 |
| Screw-threaded member | 94 |
| Longitudinal radially extending supporting vanes | 92a, 92b, 92c and 92d |
| Mid points where obtuse angles of triangles are shown | 96 and 96' |
| Distal end of hourglass-shape surface | 100, 100', 102 and 102' |
| Proximal end of hourglass-shape surface | 104, 104', 106 and 106' |
| Channel into which hourglass surface constricts | 98' |

Various modifications of the present invention will become apparent to those skilled in the art. This invention is intended to include such modification to be limited only by the scope of the claims.

What is claimed is:

1. A dimensionally stable plunger rod for use with a plunger in a cartridge or syringe barrel for manual or power-assisted withdrawal of fluid from a site or expelling fluid from the cartridge or syringe barrel, the plunger rod having first, second, third and fourth sides, a distal end and a proximal end comprising:

an end disc at the distal end;
a threaded member integral with said end disc to engage a plunger;

a thumb rest at the proximal end for facilitating exertion of external pressure on the plunger rod;

a central disc at about the mid-point between the end disc and thumb rest of the plunger rod to provide additional reinforcement between the end disc and the thumb rest;

four longitudinal radially extending rectangular vanes spaced about 90° from each other and connected to said end disc and said thumb rest;

on the first side of said plunger rod;

a first pair of longitudinal radially extending reinforcing vanes;

a second pair of longitudinal radially extending reinforcing vanes, both the first pair and the second pair of longitudinal radially extending reinforcing vanes being connected to the end disc and to the thumb rest;

on the third side opposite to said first side of said plunger rod;

a first pair of longitudinal radially extending reinforcing vanes;

a second pair of longitudinal radially extending reinforcing vanes, both of the first pair and the second pair of longitudinal radially extending reinforcing vanes being connected to said end disc, to the central disc and to the thumb rest, wherein:

each of said first pair and each of said second pair of longitudinal radially extending reinforcing vanes on the first side of said plunge rod and each of said first pair and each of said second pair of the longitudinal radially extending reinforcing vanes on the third side of said plunger rod forms an obtuse triangle with one of the longitudinal radially extending rectangular vanes, wherein the obtuse angle of said triangle is at the mid-point between said end disc and said thumb rest;

on the second side of said plunger rod;

a first pair of longitudinal radially extending supporting vanes forming a two-dimensional hourglass-shape surface extending from said end disc to the central disc and from the central disc to the thumb rest; and on the fourth side of said plunger rod;

a second pair of longitudinal radially extending supporting vanes forming a two-dimensional hourglass-shape surface extending from said end disc to the central disc and from the central disc to the thumb rest.

2. The dimensionally stable plunger rod of claim 1 wherein said four longitudinal radially extending rectangular vanes meet at a central longitudinal axis and are integral with each other at said axis.

3. The dimensionally stable plunger rod of claim 1 wherein said longitudinal radially extending reinforcing vanes and said longitudinal radially extending rectangular vanes merge into said end disc at the distal end of the plunger rod and merge into said thumb rest at the proximal end of said plunger rod and form adjacent to said end disc and to said thumb rest an X-shape pattern.

4. The dimensionally stable plunger rod of claim 1 made of a thermoplastic polymer.

5. The dimensionally stable plunger rod of claim 1 made of polypropylene, polyethylene and blends thereof.

6. The dimensionally stable plunger rod of claim 1 made of a polymeric material selected from the group consisting of polystyrenes, polyesters and polycarbonates.

7. The dimensionally stable plunger rod of claim 1 made by injection molding.

* * * * *